United States Patent [19]

Mane et al.

[11] Patent Number: 5,752,529
[45] Date of Patent: May 19, 1998

[54] TOBACCO PRODUCTS CONTAINING COOLANT COMPOSITIONS

[75] Inventors: Jean M. Mane; Jean-Louis Ponge, both of Grasse, France

[73] Assignee: V. Mane Fils S.A., France

[21] Appl. No.: 701,141

[22] Filed: Aug. 21, 1996

[51] Int. Cl.$^6$ .................................................. A26B 15/00
[52] U.S. Cl. ............................................ 131/359; 131/276
[58] Field of Search ................................ 131/274–276, 131/359, 347, 352

[56] References Cited

U.S. PATENT DOCUMENTS

| | | | |
|---|---|---|---|
| 3,111,127 | 11/1963 | Jarboe | 131/276 |
| 4,029,759 | 6/1977 | Humbert et al. | 131/275 X |
| 4,157,384 | 6/1979 | Watson et al. | 424/45 |
| 5,009,893 | 4/1991 | Cherukuri et al. | 424/440 |
| 5,451,404 | 9/1995 | Furman | 131/290 X |

FOREIGN PATENT DOCUMENTS

| | | |
|---|---|---|
| 2 339 661 | 2/1974 | Germany . |
| 26 08 226 | 9/1977 | Germany . |
| 93/23005 | 11/1993 | WIPO . |
| WO 93/25177 | 12/1993 | WIPO . |

OTHER PUBLICATIONS

"A Molecular Approach to Flavor Synthesis. I. Menthol Esters of Varying Size and Polarity", by Jabloner et al. Hercules Incorporated Research Center, Wilmington, Delaware, 1989.

*Primary Examiner*—Aaron Lewis
*Attorney, Agent, or Firm*—Larson and Taylor

[57] ABSTRACT

Tobacco products including chewing tobacco, snuff tobacco and smoking tobacco products, which contain a coolant compound selected from monomenthyl succinate, alkali metal salts of monomenthyl succinate, alkaline earth metal salts of monomenthyl succinate and mixtures thereof, are disclosed. More particularly, the disclosure relates to chewing tobacco and snuff tobacco incorporating one or more of these coolant compounds, optionally in combination with other coolants. The disclosure also relates to smoking tobacco products wherein the coolant compound is incorporated in the paper, leaf wrapper and/or filter of the smoking tobacco product and, optionally, a secondary coolant is employed in combination therewith. The tobacco products of the present invention provide a surprising, long-lasting cooling effect without enhancing the mint flavor note of menthol and tend to refresh the mouth even several minutes after first contact therewith.

21 Claims, No Drawings

TOBACCO PRODUCTS CONTAINING COOLANT COMPOSITIONS

BACKGROUND OF THE INVENTION

1. Field of the Invention

The present invention relates to smoking, chewing and snuff tobacco products which comprise coolant compositions. More particularly, the present invention relates to chewing and snuff tobacco products which incorporate a cooling composition therein as well as to smoking tobacco products which incorporate a cooling composition in the paper, leaf wrapper or filter thereof.

2. Description of the Prior Art

A variety of compounds are known which provide a cooling sensation when ingested or contacted with the body. Perhaps the best known of these compounds is menthol. It is believed that menthol acts on the cold receptors at the nerve endings in order to provide this cooling effect.

Since menthol has a strong minty odor and high relative volatility, several other coolant compounds have been developed and reported in the technical literature as potential flavorants or odorants in a variety of topical and ingestible compositions. For example, U.S. Pat. No. 5,009,893 proposes the use of menthol in combination with N-substituted-p-menthane carboxamide compounds as coolant compositions in edible products.

International Patent application publication No. WO93/23005 proposes coolant compositions for edible or topical products which comprise a ketal and a secondary coolant which may be selected from menthol, carboxamides and mixtures thereof. In addition, this patent application mentions several other references which disclose compounds which have a flavor resembling menthol including menthyl carbinol, saccharide esters of menthol and a variety of amides. Also mentioned is that 2,3-p-menthane diol has been reported as having a sharp cooling taste.

German Patent application 2 339 661 discloses aromatic compositions which include menthol or menthol esters of heterocyclic carboxylic acids. The preferred ester is menthyl-2-pyrrolidone-5-carboxylic acid ester.

German Patent application 26 08 226 discloses a composition which exhibits a physiological cooling effect. The cooling compounds disclosed include menthol esters of naturally occurring hydroxycarboxylic acids having 2–6 carbon atoms which are esterified with a $C_1$–$C_4$ alkyl group. Menthyl acetate and menthyl lactate are the most preferred cooling compounds of this disclosure. Finally, another commercially available coolant compound is 3-menthoxypropane-1,2 diol.

U.S. Pat. No. 3,111,127 (Jarboe) discloses smoking tobacco products which incorporate a monoester of synthetic or natural menthol and a saturated or unsaturated aliphatic or aromatic polycarboxylic acid or a substituted analog of such an acid. These tobacco products were evaluated and observed to burn slower at smolder than a comparable control product, to have increased firmness, and to require more puffs under a controlled smoking regime. Further, when tested organoleptically, these products were found to deliver smoke having the pleasing and cooling taste and aroma characteristic of menthol. Among the polycarboxylic acid esters are mentioned methylsuccinic acid ester, mono menthylsuccinate, monomenthyl-α,α-dimethylsuccinate and mono menthol-methylsuccinate.

Thus, a variety of compounds are known which provide cooling properties and are useful in a wide variety of products including smoking tobacco. However, there is a still a need to improve on the taste perception and cooling effect associated with smoking tobacco products, chewing tobacco and snuff.

Accordingly, it is an object of the present invention to provide improved smoking tobacco products, chewing tobacco and snuff having a pleasant, refreshing and long lasting cooling effect.

It is a further object of the present invention to provide smoking tobacco products, chewing tobacco and snuff having a unique cooling sensation and taste perception.

It is a still further object of the present invention to provide smoking tobacco products, chewing tobacco and snuff compositions which include two or more cooling agents which provide a complementary cooling sensation and taste perception.

These and other objects of the present invention will be apparent from the summary and detailed descriptions which follow.

SUMMARY OF THE INVENTION

The present invention relates, in a first aspect, to a chewing or snuff tobacco product which comprises at least one of chewing tobacco or snuff tobacco and an effective amount of a coolant selected from monomenthyl succinate, alkali metal salts of monomenthyl succinate, alkaline earth metal salts of monomenthyl succinate and mixtures thereof.

In a second aspect, the present invention relates to a smoking tobacco product which includes smoking tobacco and a combustible paper or leaf wrapper in which the smoking tobacco is housed. The combustible paper or leaf wrapper has incorporated therein an effective amount of a coolant selected from monomenthyl succinate, alkali metal salts of monomenthyl succinate, alkaline earth metal salts of monomenthyl succinate and mixtures thereof.

In a third aspect, the present invention relates to a smoking tobacco product which includes smoking tobacco, a combustible paper or leaf wrapper in which the smoking tobacco is housed and a filter. The filter has incorporated therein an effective amount of a coolant selected from monomenthyl succinate, alkali metal salts of monomenthyl succinate, alkaline earth metal salts of monomenthyl succinate and mixtures thereof.

Monomenthyl succinate is a known compound having Chemical Abstracts no. 77341-67-4. The article, "A Molecular Approach to Flavor Synthesis. I. Menthol Esters of Varying Size and Polarity," Jabloner, H. and Dunbar, B. I., *J. of Polymer Science*, Vol. 18, pages 2933–40 (1980) discloses a method for the synthesis of monomenthyl succinate as well as monomenthyl sodium succinate and other menthol esters derived from monomenthyl succinate. Solutions of 5% by weight of several of these menthol esters in mineral oil or water were tasted by a nine person taste panel. 5% of dimethyl succinate in mineral oil was found to be odorless and tasteless. 5% sodium monomenthyl succinate in water was found to be vile and bitter. Monomenthyl succinate itself was not tasted. The present inventors have surprisingly found that monomenthyl succinate, alkali metal salts of monomenthyl succinate, alkaline earth metal salts of monomenthyl succinate and mixtures thereof used in a variety of tobacco products at low concentrations give a pleasing, refreshing and long-lasting cooling effect rather than the vile and bitter taste observed by the taste panel in the Jabloner article.

DETAILED DESCRIPTION OF THE PREFERRED EMBODIMENTS

The present invention relates to tobacco products which have associated therewith an effective amount of a cooling compound selected from monomenthyl succinate, alkali metal salts of monomenthyl succinate, alkaline earth metal salts of monomenthyl succinate and mixtures thereof (hereinafter collectively referred to "succinate-based coolant compounds").

More preferably, the succinate-based coolant compounds employed in the tobacco products of the present invention is selected from monomenthyl succinate, monomenthyl sodium succinate, monomenthyl potassium succinate, monomenthyl lithium succinate, monomenthyl calcium succinate, monomenthyl magnesium succinate and monomenthyl barium succinate, as well as mixtures thereof.

The succinate-based coolant compounds are incorporated in a variety of tobacco products in accordance with the present invention. In a first aspect, the succinate-based coolant compounds are incorporated into chewing tobacco or snuff.

In a second aspect, the succinate-based coolant compounds are associated with smoking tobacco products either by incorporating the succinate-based coolant compounds into the combustible paper, leaf wrapper or filter of the smoking tobacco products or by applying the succinate-based coolant compounds to the paper, leaf wrapper and/or filter of smoking tobacco products by application to the surface thereof.

By tobacco products is meant products such as cigarettes, cigars, chewing tobacco and snuff which include as a component tobacco, or a tobacco derivative product. For example, clove cigarettes and cigars as well as flavored chewing tobaccos and the like are included within the scope of tobacco products in accordance with the present invention. Further, snuff tobacco products include both the form of snuff that is inhaled through the nose as well as what is known as moist snuff which is snuff that is placed in the mouth in either a pellet form or contained in a sachet made of high porosity paper. In the case of the latter form of moist snuff, the succinate-based coolant compounds may be applied to the porous paper of the sachet rather than directly to the moist snuff.

It is has been surprisingly found that the succinate-based coolant compounds, when used in low concentrations provide a pleasing cooling, or long-lasting cooling effect without the bitterness which would be expected from the prior art. Further, the succinate-based coolant compounds do not develop a strong minty taste as do other coolants such as menthol.

The succinate-based coolant compounds provide a cooling effect in a different area of the mouth and throat than, for example, menthol or carboxamide-based coolant compounds. As a result, the succinate-based coolant compounds of the present invention provide a complementary of synergistic effect when combined with at least one secondary cooling compound in a tobacco product.

The succinate-based coolant compounds of the present invention also provide a refreshing aftertaste when employed in certain tobacco products. Further, when used in combination with material such as menthol, the succinate-based coolant compounds do not enhance the minty flavor which is associated with menthol but rather provide a complementary cooling effect without undesirably enhancing the mint taste.

In making the tobacco products of the present invention, the coolant compound can be employed in the form of a coolant composition or the coolant compound or composition may be incorporated into a carrier material which may be inert or contain other active ingredients of the end use composition. A wide variety of carrier materials can be employed including, for example, polar solvents, oils, fats, finely divided solids, maltodextrins, cyclodextrins, gums, natural or synthetic resins and any other known carrier materials for such compositions.

The amount of coolant composition incorporated in each of the tobacco products of the invention will vary depending upon the particular compound, the degree of cooling effect desired and the strength of other coolants in the composition. Typically, the succinate-based coolant compound will make up from 0.01–0.5% by weight of the tobacco product. More preferably, the succinate-based coolant compound makes up 0.02–0.3% by weight, based on the total weight of the tobacco product.

The succinate-based coolant compounds are applied to the tobacco products in any conventional manner such as by spraying, brushing or injection, for example. When applied to the combustible paper, leaf wrapper or the filter of smoking tobacco products, the succinate-based coolant compounds may be sprayed or brushed on or, in the case of filters, may be injected in the filter. Any other suitable means for incorporated the succinate-based coolant compounds and/or solutions or dispersions thereof, into or on the chewing or snuff tobacco or the paper, leaf wrapper or filter, can be employed.

The present invention also relates to tobacco products including a combination of a primary cooling agent selected from monomenthyl succinate, alkali metal salts of monomenthyl succinate, alkaline earth metal salts of monomenthyl succinate and mixtures thereof, with at least one secondary coolant component.

Secondary coolant components which may be used in combination with the primary coolant of the present invention include menthol, carboxamides, ketals, menthyl acetate, menthyl lactate, 3-menthoxypropane-1,2 diol and mixtures thereof. The carboxamide and ketal coolant compositions are known from the prior art and can be found, for example, in U.S. Pat. No. 5,009,893 and international patent application publication No. WO-93/23005, the disclosures of which are hereby incorporated by reference. The remaining secondary coolants are known cooling agents, some of which are commercially available.

More particularly, the carboxamide secondary coolants are selected from N-substituted-p-menthane-3-carboxamides of the formula:

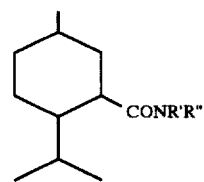

wherein R', when taken separately, is hydrogen or an aliphatic radical containing up to 25 carbon atoms; R" when taken separately is hydroxy or an aliphatic radical containing up to 25 carbon atoms, with the proviso that when R' is hydrogen R" may also be an aryl radical of up to 10 carbon atoms and selected from the group consisting of substituted phenyl, phenylalkyl, substituted phenylalkyl, naphthyl, substituted naphthyl and pyridyl; and R' and R", when taken together with the nitrogen atom to which they are attached, represent a cyclic or heterocylic group of up to 25 carbon atoms;

acyclic tertiary and secondary carboxamides of the formula:

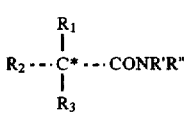

where R' and R", when taken separately, are each hydrogen, $C_1$–$C_5$ alkyl or $C_1$–$C_8$ hydroxyalkyl and provide a total of no more than 8 carbon atoms, with the proviso that when R' is hydrogen R" may also be alkylcarboxyalkyl of up to 6 carbon atoms; R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen; $R_1$ is hydrogen or $C_1$–$C_5$ alkyl; and $R_2$ and $R_3$ are each $C_1$–$C_5$ alkyl; with the provisos that (i) $R_1$, $R_2$, and $R_3$ together provide a total of at least 5 carbon atoms, preferably from 5–10 carbon atoms; and (ii) when $R_1$ is hydrogen, $R_2$ is $C_2$–$C_5$ alkyl and $R_3$ is $C_2$–$C_5$ alkyl and at least one of $R_2$ and $R_3$ is branched, preferably in an alpha or beta position relative to the carbon atom marked (*) in the formula; and mixtures thereof.

The ketal coolant compositions may be represented by the formula:

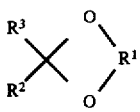

in which $R^1$ represents a $C_2$–$C_6$-alkylene radical having at least 1, but not more than 3, hydroxyl group(s), and either $R^2$ and $R^3$ independently of one another represent $C_1$–$C_{10}$-alkyl which is optionally substituted by 1 to 3 radicals selected from the group comprising hydroxyl, amino and halogen, $C_5$–$C_7$-cycloalkyl, preferably cyclohexyl, and $C_6$–$C_{12}$-aryl, preferably phenyl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5–7 member ring, optionally substituted by $C_1$–$C_6$-alkyl groups.

The relative amounts of the primary and secondary coolants in the composition of the present invention may be varied over a wide range of compositions depending upon the particular level of cooling desired. For example, when the strong minty taste of menthol is desirable, a combination of a large quantity of menthol with a relatively small quantity of the succinate-based coolant compounds of the present invention may be desirable. Further, the secondary coolant may be incorporated in the tobacco or, in the case of smoking tobacco products, the secondary coolant may be incorporated in either the tobacco or in the paper, leaf wrapper or filter along with the primary coolant. Other potential combinations of the primary coolant with secondary coolant components will be apparent to the man of skill in the art.

Generally, the level of the secondary coolant compounds in the tobacco products of the present invention is from about 10% by weight to about 700% by weight, more preferably from about 20% by weight to about 650% by weight, and most preferably from about 30% by weight to about 500% by weight, based on the weight of the primary coolant. Typically, the secondary coolant may be applied to or incorporated in the tobacco product in the same manner as is detailed above for the primary coolant or in any other conventional manner.

The invention will be further illustrated by the following examples.

EXAMPLES 1–4 AND COMPARATIVE EXAMPLES A–B

Mono Menthylsuccinate in Cigarette Filters Combined With Menthol in the Tobacco

The tobacco rods of some regular international blended cigarettes and of flue-cured cigarettes were each injected with 20 µl of a 10% solution of menthol crystals in ethanol. The menthol-injected cigarettes were then divided into five sets. 20 µl, 30 µl, 40 µl, and 50 µl of a 1% solution of mono menthylsuccinate in triacetine were injected into the filter of the first four sets of cigarettes with the fifth set of cigarettes being used as a control. Each set of cigarettes includes a control with no menthol and no mono menthylsuccinate, a cigarette including only menthol, a cigarette including only mono menthylsuccinate and a cigarette including both menthol and mono menthylsuccinate.

An expert smoking panel (ESP) lighted, smoked and tasted each set of the test cigarettes and found that at a level of 0.2 µl of mono menthylsuccinate and no menthol, there was no cooling effect. At 0.3 µl of mono menthylsuccinate with no menthol a slight cooling effect was noted. At a level of 0.4 µl of mono menthylsuccinate a strong cooling effect with a refreshing aftertaste was noted by the ESP. Further, in combination with menthol in the tobacco at this level, no enhancement of the "mint" flavor note of the menthol by the mono menthylsuccinate was detected by the ESP. At a level of 0.5 µl of mono menthylsuccinate the cooling effect was even more evident to the ESP and still no enhancement of the "mint" flavor note of menthol was noted. However, a minor increase in irritation was experienced by the ESP at this level of mono menthysuccinate.

The ESP concluded that the mono menthylsuccinate injected in the filter of cigarettes had a cooling effect on the smoke and provided a lingering refreshing character in the mouth without significantly altering the flavor note of the menthol in the tobacco.

EXAMPLE 5

Mono Menthylsuccinate Used With WS3™ Coolant in Filters and Menthol in the Tobacco Rod The tobacco rod of selected cigarettes as in Examples 1–4 above was injected with 20 µl of a 10% solution of menthol crystals in ethanol. The menthol injected cigarettes were divided into two sets. 45 µl of a 1% solution of mono menthylsuccinate in triacetine and 15 µl of a 1% solution of WS3™ in triacetine were injected into the filter of one set of the cigarettes containing menthol.

The ESP observed an intense cooling effect and a slight enhancement of the mint and aromatic flavor notes of the menthol, as compared to the menthol-containing control. No increase in irritation was found. The panel concluded that at these levels, a synergistic effect occurred between the two cooling agents.

EXAMPLES 6–7

Mono Menthylsuccinate in Chewing Tobacco and Snuff Tobacco 0.08% and 0.12% by weight of mono menthylsuccinate were added by injection to chewing tobacco using a 10 µl gas chromatography syringe and the same levels of mono menthylsuccinate were added to snuff by spraying using a thin atomizer.

Each sample of the tobacco was kept in the mouth of the ESP members for a one minute test period after which the mouth was cleaned with pure water and a waiting period of five minutes was observed before starting a new evaluation.

At a level of 0.08% by weight, a refreshing effect was observed by the ESP after a period of 2–3 minutes. At 0.12% by weight an even higher intensity of cooling was observed approximately two minutes after the tobacco was removed from the mouth, whereby the interior of the mouth was judged as being cleaner. Also, the ESP concluded that a more pleasant refreshing aftertaste was present. The aftertaste lasted for up to five minutes following the removal of the tobacco from the mouth.

EXAMPLES 8–9

Mono Menthylsuccinate in Filter Tipping Paper of Indonesian Cigarettes

10 μl and 20 μl of a 1% solution of mono menthylsuccinate in triacetine was distributed in the form of a thin film applied with a soft brush over the first third of the mouth end of the filter tipping paper of different types of Kretek cigarettes obtained from the Indonesian market.

At 0.10 μl of mono menthylsuccinate, the ESP found a slight refreshing effect on the lips after 2–3 minutes following insertion of the Kretek cigarette in the mouth. At 20 μl the cooling effect associated with a refreshing character started approximately one minute after insertion of the Kretek cigarette in the mouth and lasted for up to five minutes on the lips and inner part of the mouth. The ESP concluded that the mono menthylsuccinate had an effect that can be efficacious in retaining a refreshing, clean character on the lips and inner part of the mouth when applied on the mouth end of a Kretek cigarette.

The foregoing examples have been presented for the purpose of illustration and description only and are not to be construed as limiting the invention in any way. The scope of the invention is to be determined by the claims appended hereto.

We claim:

1. A chewing or snuff tobacco product which comprises a tobacco selected from the group consisting of chewing tobacco and snuff tobacco; and an effective amount of a coolant incorporated in said tobacco such that the coolant note is tasted in the absence of combustion, said coolant being selected from the group consisting of monomenthyl succinate, alkali metal salts of monomenthyl succinate, alkaline earth metal salts of monomenthyl succinate and mixtures thereof.

2. A tobacco product as claimed in claim 1 which comprises from 0.01–0.5% by weight, based on the total weight of the tobacco product, of said coolant.

3. A tobacco product as claimed in claim 1 further comprising at least one secondary coolant component.

4. A tobacco product as claimed in claim 3 where the secondary coolant component is selected from the group consisting of menthol, carboximides, ketals, menthyl acetate, menthyl lactate, 3-methoxypropane-1,2 diol and mixtures thereof.

5. A tobacco product as claimed in claim 4 wherein the carboximide coolant component is selected from the group consisting of:

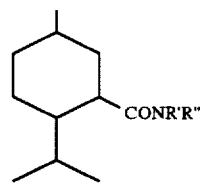

where R', when taken separately, is hydrogen or an aliphatic radical containing up to 25 carbon atoms; R" when taken separately is hydroxy, or an aliphatic radical containing up to 25 carbon atoms, with the proviso that when R' is hydrogen, R" may also be an aryl radical of up to 10 carbon atoms selected from the group consisting of substituted phenyl, phenalkyl, substituted phenalkyl, naphthyl, substituted naphthyl and pyridyl; and R' and R", when taken together with the nitrogen atom to which they are attached, represent a cyclic or heterocyclic group of up to 25 carbon atoms;

acyclic tertiary and secondary carboximides of the formula:

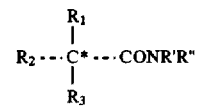

where R' and R", when taken separately, are each hydrogen, $C_1$–$C_5$ alkyl or $C_1$–$C_8$ hydroxyalkyl and provide a total of no more than 8 carbon atoms, with the proviso that when R' is hydrogen R" may also be alkylcarboxyalkyl of up to 6 carbon atoms; R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen;

$R_1$ is hydrogen or $C_1$–$C_5$ alkyl; and $R_2$ and $R_3$ are each $C_1$–$C_5$ alkyl; with the provisos that (i) $R_1$, $R_2$, and $R_3$ together provide a total of at least 5 carbon atoms; and (ii) when $R_1$ is hydrogen, $R_2$ is $C_2$–$C_5$ alkyl and $R_3$ is $C_2$–$C_5$ alkyl and at least one of $R_2$ and $R_3$ is branched, and mixtures thereof.

6. A tobacco product as claimed in claim 4 wherein the ketal coolant component is selected from the group consisting of:

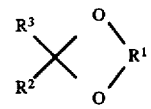

in which $R^1$ represents a $C_2$–$C_6$-alkylene radical having at least 1, but not more than 3, hydroxyl group(s), and either $R^2$ and $R^3$ independently of one another represent $C_1$–$C_{10}$-alkyl which is optionally substituted by 1 to 3 radicals selected from the group comprising hydroxyl, amino, halogen, $C_5$–$C_7$-cycloalkyl, $C_6$–$C_{12}$-aryl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5–7 member ring, optionally substituted by $C_1$–$C_6$-alkyl groups.

7. A tobacco product as claimed in claim 1 wherein the coolant is selected from the group consisting of monomenthyl succinate and monomenthyl sodium succinate.

8. A smoking tobacco product which comprises smoking tobacco and a combustible paper or leaf wrapper in which the smoking tobacco is housed, said combustible paper or leaf wrapper comprising an effective amount of a coolant incorporated in said paper or leaf wrapper such that the coolant note is tasted in the absence of combustion, said coolant being selected from the group consisting of monomenthyl succinate, alkali metal salts of monomenthyl succinate, alkaline earth metal salts of monomenthyl succinate and mixtures thereof.

9. A smoking tobacco product as claimed in claim 8 which comprises from 0.01–0.5% by weight, based on the total weight of the smoking tobacco product, of said coolant.

10. A smoking tobacco product as claimed in claim 8 further comprising at least one secondary coolant component.

11. A smoking tobacco product as claimed in claim 10 where the secondary coolant component is selected from the group consisting of menthol, carboximides, ketals, menthyl acetate, menthyl lactate, 3-methoxypropane-1,2 diol and mixtures thereof.

12. A smoking tobacco product as claimed in claim 11 wherein the carboximide coolant component is selected from the group consisting of:

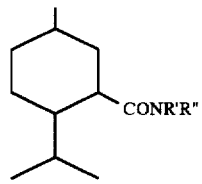

where R', when taken separately, is hydrogen or an aliphatic radical containing up to 25 carbon atoms; R" when taken separately is hydroxy, or an aliphatic radical containing up to 25 carbon atoms, with the proviso that when R' is hydrogen, R" may also be an aryl radical of up to 10 carbon atoms selected from the group consisting of substituted phenyl, phenalkyl, substituted phenalkyl, naphthyl, substituted naphthyl and pyridyl; and R' and R", when taken together with the nitrogen atom to which they are attached, represent a cyclic or heterocyclic group of up to 25 carbon atoms;

acyclic tertiary and secondary carboximides of the formula:

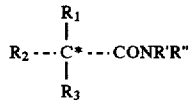

where R' and R", when taken separately, are each hydrogen, $C_1$–$C_5$ alkyl or $C_1$–$C_8$ hydroxyalkyl and provide a total of no more than 8 carbon atoms, with the proviso that when R' is hydrogen R" may also be alkylcarboxyalkyl of up to 6 carbon atoms; R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen; $R_1$ is hydrogen or $C_1$–$C_5$ alkyl; and $R_2$ and $R_3$ are each $C_1$–$C_5$ alkyl; with the provisos that (i) $R_1$, $R_2$, and $R_3$ together provide a total of at least 5 carbon atoms; and (ii) when $R_1$ is hydrogen, $R_2$ is $C_2$–$C_5$ alkyl and $R_3$ is $C_2$–$C_5$ alkyl and at least one of $R_2$ and $R_3$ is branched, and mixtures thereof.

13. A smoking tobacco product as claimed in claim 11 wherein the ketal coolant component is selected from the group consisting of:

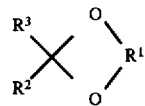

in which $R^1$ represents a $C_2$–$C_6$-alkylene radical having at least 1, but not more than 3, hydroxyl group(s), and either $R^2$ and $R^3$ independently of one another represent $C_1$–$C_{10}$-alkyl which is optionally substituted by 1 to 3 radicals selected from the group comprising hydroxyl, amino, halogen, $C_5$–$C_7$-cycloalkyl, $C_6$–$C_{12}$-aryl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5–7 member ring, optionally substituted by $C_1$–$C_6$-alkyl groups.

14. A smoking tobacco product as claimed in claim 8 wherein the coolant is selected from the group consisting of monomenthyl succinate and monomenthyl sodium succinate.

15. A smoking tobacco product which comprises smoking tobacco, a combustible paper or leaf wrapper in which the smoking tobacco is housed and a filter, said filter comprising an effective amount of a coolant incorporated in said filter such that the coolant note is tasted in the absence of combustion, said coolant being selected from the group consisting of monomenthyl succinate, alkali metal salts of monomenthyl succinate, alkaline earth metal salts of monomenthyl succinate and mixtures thereof.

16. A smoking tobacco product as claimed in claim 15 which comprises from 0.02–0.06% by weight, based on the total weight of the smoking tobacco product, of said coolant.

17. A smoking tobacco product as claimed in claim 15 further comprising at least one secondary coolant component.

18. A smoking tobacco product as claimed in claim 17 where the secondary coolant component is selected from the group consisting of menthol, carboximides, ketals, menthyl acetate, menthyl lactate, 3-methoxypropane-1,2 diol and mixtures thereof.

19. A smoking tobacco product as claimed in claim 18 wherein the carboximide coolant component is selected from the group consisting of:

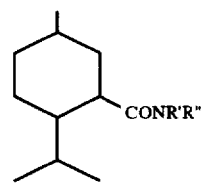

where R', when taken separately, is hydrogen or an aliphatic radical containing up to 25 carbon atoms; R" when taken separately is hydroxy, or an aliphatic radical containing up to 25 carbon atoms, with the proviso that when R' is hydrogen, R" may also be an aryl radical of up to 10 carbon atoms selected from the group consisting of substituted phenyl, phenalkyl, substituted phenalkyl, naphthyl, substituted naphthyl and pyridyl; and R' and R", when taken together with the nitrogen atom to which they are attached, represent a cyclic or heterocyclic group of up to 25 carbon atoms;

acyclic tertiary and secondary carboximides of the formula:

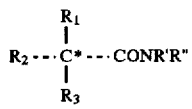

where R' and R", when taken separately, are each hydrogen, $C_1$–$C_5$ alkyl or $C_1$–$C_8$ hydroxyalkyl and provide a total of no more than 8 carbon atoms, with the proviso that when R' is hydrogen R" may also be alkylcarboxyalkyl of up to 6 carbon atoms; R' and R", when taken together, represent an alkylene group of up to 6 carbon atoms, the opposite ends of which group are attached to the amide nitrogen atom thereby to form a nitrogen heterocycle, the carbon chain of which may optionally be interrupted by oxygen; $R_1$ is hydrogen or $C_1$–$C_5$ alkyl; and $R_2$ and $R_3$ are each $C_1$–$C_5$ alkyl; with the provisos that (i) $R_1$, $R_2$, and $R_3$ together provide a total of at least 5 carbon atoms; and (ii) when $R_1$ is hydrogen, $R_2$ is $C_2$–$C_5$ alkyl and $R_3$ is $C_2$–$C_5$ alkyl and at least one of $R_2$ and $R_3$ is branched and mixtures thereof.

20. A smoking tobacco product as claimed in claim 18 wherein the ketal coolant component is selected from the group consisting of:

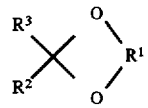

in which $R^1$ represents a $C_2$–$C_6$-alkylene radical having at least 1, but not more than 3, hydroxyl group(s), and either $R^2$ and $R^3$ independently of one another represent $C_1$–$C_{10}$-alkyl which is optionally substituted by 1 to 3 radicals selected from the group comprising hydroxyl, amino, halogen, $C_5$–$C_7$-cycloalkyl, $C_6$–$C_{12}$-aryl, with the proviso that the total of the C atoms of $R^2$ and $R^3$ is not less than 3, or $R^2$ and $R^3$ together represent an alkylene radical which, together with the carbon atom which carries the radicals $R^2$ and $R^3$, forms a 5–7 member ring, optionally substituted by $C_1$–$C_6$-alkyl groups.

21. A smoking tobacco product as claimed in claim 15 wherein the coolant is selected from the group consisting of monomenthyl succinate and monomenthyl sodium succinate.

* * * * *